United States Patent
Skog et al.

(10) Patent No.: US 6,397,846 B1
(45) Date of Patent: Jun. 4, 2002

(54) MOISTURE BARRIER AND BACTERIA BARRIER FOR MEDICAL COMPONENTS

(75) Inventors: Göran Skog, Bromma; Lars Wallén, Spånga; Carl-Erik Arvidsson, Solna, all of (SE)

(73) Assignee: Siemens-Elema AB, Solna (SE)

(*) Notice: Subject to any disclaimer, the term of this patent is extended or adjusted under 35 U.S.C. 154(b) by 0 days.

(21) Appl. No.: 09/382,337

(22) Filed: Aug. 25, 1999

(30) Foreign Application Priority Data

Sep. 9, 1998 (SE) .............................................. 9803047

(51) Int. Cl.[7] .............................................. A62B 23/02
(52) U.S. Cl. .............................. 128/205.29; 55/DIG. 35
(58) Field of Search ........................... 128/205.29, 909, 128/201.13, 204.22, 204.23; 600/530, 531, 532; 55/DIG. 35, 484, 502

(56) References Cited

U.S. PATENT DOCUMENTS

| 923,776 A | * | 6/1909 | Danielewicz |
| 5,293,875 A | * | 3/1994 | Stone .......................... 128/719 |
| 5,357,971 A | * | 10/1994 | Sheehan et al. ............. 128/719 |
| 5,361,771 A | * | 11/1994 | Craine et al. ................ 128/719 |
| 5,419,326 A | | 5/1995 | Harnoncourt |
| 5,647,370 A | | 7/1997 | Harnoncourt |

* cited by examiner

Primary Examiner—John G. Weiss
Assistant Examiner—Mital Patel
(74) Attorney, Agent, or Firm—Schiff Hardin & Waite

(57) ABSTRACT

An arrangement to provide a moisture barrier and bacteria barrier for various medical components that is connected to a measuring tube, arranged in the flow paths of a respirator is simple and inexpensive and exchangeable and does not cause a flow resistance in the flow paths of the respirator. A carrier carries at least two moisture barriers and bacteria barriers such that one barrier, given a carrier introduced in the respirator, is arranged exactly in front of each component.

6 Claims, 1 Drawing Sheet

MOISTURE BARRIER AND BACTERIA BARRIER FOR MEDICAL COMPONENTS

BACKGROUND OF THE INVENTION

1. Field of the Invention

The present invention is directed to a moisture barrier and bacteria barrier, which is connected to a measuring tube that is arranged in the flow paths of a respirator, for protecting medical components in communication with the measuring tube.

2. Description of the Prior Art

In order to be able to monitor and control a respirator, a number of parameters, preferably at the expiration side, are measured using medical components. The medical components are preferably arranged in a fluid-tight manner in a unit, which is connected at the measuring tube. It is known to connect a moisture barrier and bacteria barrier to the entrance of the measuring tube in the form of a filter, which is arranged in a mouthpiece made of plastic, in order to protect the medical components against "contaminations" in the breathing air, such as drugs and body fluids. Thus, an autoclaving of the medical components, most of which are sensitive and would become uncalibrated or damaged due to autoclaving can be avoided. The mouthpiece made of plastic and the filter are for the most part formed of a disposable material that is thrown away after each utilization and these are replaced with a new mouthpiece with filter when a new patient is connected to the respirator. This disposable product entails relatively high costs for the hospital and also has environmental concerns associated therewith. Moreover, the filter represents a specific flow resistance in the expiration line. When the filter is used for a longer period, it can become occluded; thereby producing a flow resistance that is excessively high. This, in turn, can lead to an increased pressure in the lungs and a greater risk for lung or respiratory injury.

European Application 0 841 083 proposes a solution for this problem in a method and an arrangement for the functional control of filters in order to optimize the period of use without the risk of the patient-related problems.

U.S. Pat. No. 5,419,326 describes an ultrasound fluxmeter in which the transmitter and the receiver are arranged at a distance from each other along a measuring path, which extends obliquely relative to the axis of a tubular measuring chamber. A sterile insertion tube is introduced into the measuring chamber for each new patient. The sterile tube is provided with measuring windows that are adapted to lie above the openings in the measuring chamber. Membranes are arranged in the measuring windows; these membranes being permeable to ultrasound signals but impermeable to moisture and bacteria, so that the ultrasound signals can pass along the measuring path through the sterile insertion tube. Autoclaving the fluxmeter after each use thus is avoided, which is an advantage since the ultrasound transmitting unit and the reception unit, in particular, are sensitive parts in the fluxmeter. The membranes are arranged at a distance from the ultrasound transmitting heads and reception heads. The signals must initially pass through the membrane and then a relatively large air gap, so that the ultrasound signals can reach the transmitting unit, or the reception unit. This passage from the membrane to a relatively large air gap can lead to a high acoustic impedance, i.e., a high sound wave reflection. This can lead to relatively high acoustic losses, so that a low sound signal, which cannot be detected, reaches the reception head. One response this problem is to dispose the membrane closely at the ultrasound transmitting heads and reception heads. Given such a solution, which is described in the Swedish patent application 9801007 (corresponding to co-pending U.S. application Ser. No. 09/274,862, filed Mar. 23, 1999 entitled "Device for Measuring a Gas Flow," Wallen et al., assigned to the same Assignee as the present application), the membranes are not mounted at a sterile insertion tube but are directly fastened at the transmitting heads and reception heads.

There are other medical components which also require the membrane or the filter to be disposed close to the component in order to receive the best possible measuring result. Given the arrangement described in U.S. Pat. No. 5,419,326, it can be difficult, due to the wall thickness of the measuring chamber, to closely mount the barrier relative to a medical component, since the carrier for the barrier must be pushed into and placed in the measuring chamber. Although two barriers are attached at the sterile tube, these two barriers are merely provided for one single medical component.

SUMMARY OF THE INVENTION

An object of the present invention is to provide a relatively simple and inexpensive moisture barrier and bacteria barrier, which can be exchanged and does not cause a flow resistance in the flow paths of a respirator, for protecting medical components.

This object is inventively achieved in a carrier on which at least two barriers (which can be moisture or bacteria barriers) are mounted such that one barrier is arranged exactly in front of each medical component, when the carrier is introduced into the respirator. A filter at the entrance of the measuring tube, with the aforementioned disadvantages associated therewith, is avoided. By means of the invention, each medical component that is connected to the measuring tube can have an individually adapted barrier. If required, the barriers can be closely applied at the component or can be mounted so as to be spaced from the component. Because the barriers are mounted at a common carrier, they can be exchanged in a fast and simple manner, if required. Since a carrier of this type is relatively simple in its construction, the manufacturing costs can be kept low.

In a respirator with a measuring tube in which firmly mounted components are arranged, the inventive carrier can be attached between the measuring tube and the unit in which the components are mounted. By the placement of the carrier, the barriers can, if required, be closely disposed relative to a component, unlike the aforementioned arrangement described in U.S. Pat. No. 5,419,326.

Since the medical components in the unit are usually arranged in succession, the carrier preferably has an elongated form. The cross-section profile of the carrier is preferably adapted to the outside profile of the measuring tube. The carrier is preferably manufactured from a plastic material.

In an embodiment of the invention the peripheral surface of the carrier is provided with a seal that can be placed adjacent the measuring tube given an introduced carrier. It is thus assured that gas does not seep out of the measuring tube.

According to the invention, the barriers are filters and/or membranes.

As already mentioned, the carrier is inventively exchangeable. Thus, a new carrier can be introduced before each new patient.

DESCRIPTION OF THE PREFERRED EMBODIMENTS

Figure 1:
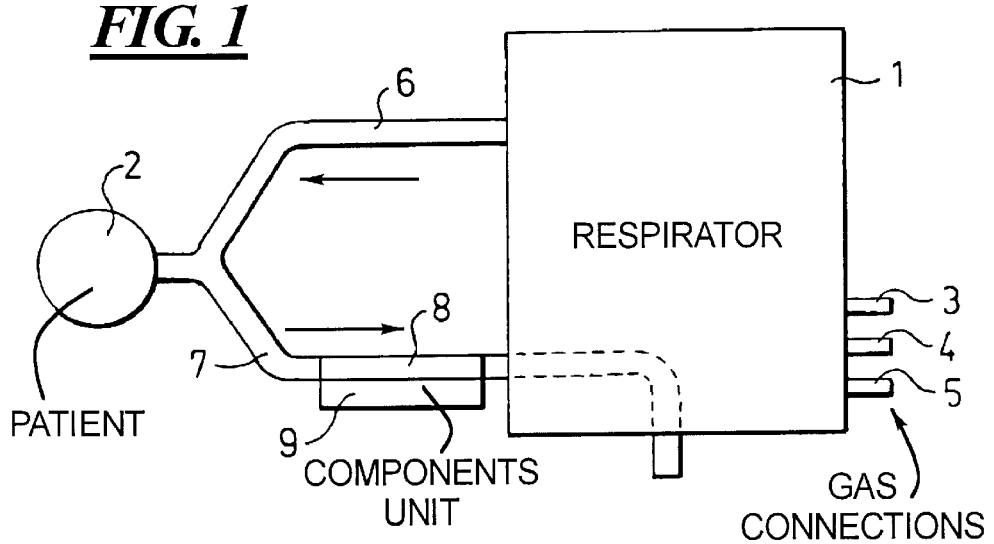
FIG. 1 is a schematic illustration of a respirator with a measuring tube and a unit for medical components that are connected to the expiration line.

FIG. 1 shows a respirator to which a patient is connected in order to be supplied with breathing gas. The gases that together form the breathing gas are supplied to the ventilator 1 via gas connections 3, 4 and 5. Given an inspiration, the breathing gas is supplied to the patient 2 via an inspiration line 6. Given an expiration, the breathing gas is conducted from the patient 2 through an expiration line 7 and is discharged into the environment via the respirator 1, primarily to a collecting container that is not shown. A measuring tube 8, which is connected to a unit 9 that contains medical components, is arranged in the expiration line 7.

Figure 2:
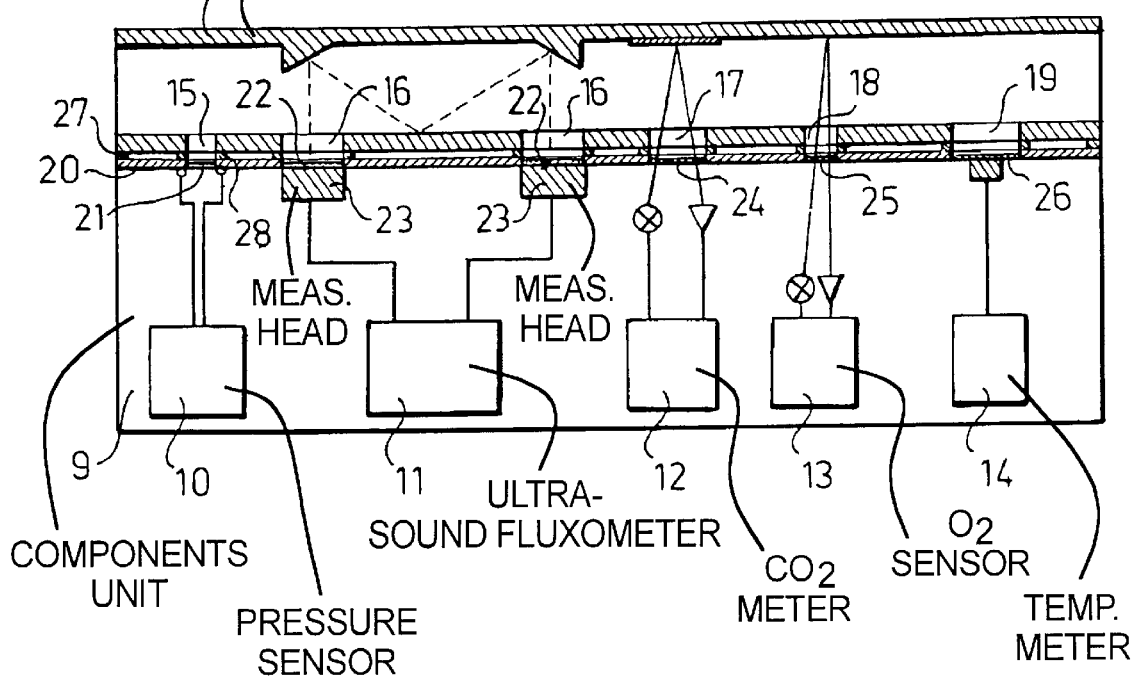
FIG. 2 shows a measuring tube in longitudinal section, a unit with schematically illustrated medical components, and a carrier therebetween for producing a moisture barrier and a bacteria barrier according to the invention.

FIG. 2 shows the measuring tube 8 and the unit 9 in a larger scale compared to FIG. 1. The medical components are firmly arranged in the unit 9. In this exemplary embodiment, the unit 9 includes a pressure transducer sensor 10, an ultrasound fluxmeter 11, a carbon dioxide meter 12, an oxygen sensor 13 and a temperature meter 14. The components 10 through 14 are arranged in succession. The components 10 through 14 are in communication with the interior of the measuring tube 8 via openings 15 through 19 in the wall of the measuring tube 8. In order to avoid that the components 10 through 14 becoming contaminated by the "contaminated" expiration air, moisture barriers and bacteria barriers are arranged between the measuring tube 8 and the components 10 through 14. The barriers are attached on a common carrier 20, each in the form of a disc that is made of plastic for example, such that each barrier is respectively arranged exactly in front of each component 10 through 14. Thus, the barrier is a bacteria filter for the pressure transducer 10, is a foil 22, preferably adjacent the measuring heads 23 in a close fashion, for the ultrasound fluxmeter 11, is a window for the carbon dioxide meter 12, is a transparent foil 25 for the oxygen sensor 13 and is a metal foil 26 for the temperature meter 14.

Given exchange of the carrier 20, the unit 9 is preferably removed from the measuring tube 8. Subsequently, the carrier 9 is removed with its barriers 21, 22, 24, 25, 26 from the measuring tube 8 and is exchanged with a new carrier 20 that is suitable for the purpose. Subsequently, the unit 9 with the medical components 10 through 14 is again introduced. The peripheral surface of the carrier 20 is preferably provided with a seal 27 that is adjacent the measuring tube 8 given an introduced carrier. The seal 27 is intended to prevent gas from seeping out of the measuring tube 8. In this exemplary embodiment, sealing rings are also arranged around the openings 15 through 19. In FIG. 2, only one sealing ring has a reference number 28, this being for the opening 15.

Figure 3:
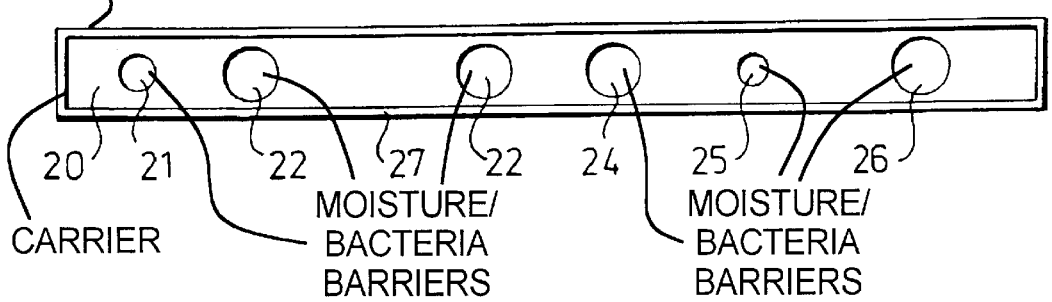
FIG. 3 shows the carrier according to FIG. 2 in a plan view.

FIG. 3, which is a plan view of the carrier 20, shows that the barriers 21,22, 24, 25, 26 are arranged in succession. FIG. 3 also shows the seal 27 that is arranged along the peripheral surface of the carrier 20.

In the framework of the invention, more or fewer medical components than the mentioned ones can be contained in the unit 9. Further, it is not necessary that these components be arranged in succession, as it is shown in the example. According to the invention, it is important that the exchangeable carrier 20 carry moisture barriers and bacteria barriers that are arranged such that each is respectively arranged exactly in front of a component, given a carrier 20 that is introduced into the respirator. By the application of the carrier 20 between the measuring tube 8 and the unit 9, the barriers can preferably be attached closely at the respective medical components, if necessary.

The invention avoids a flow resistance arising in the expiration flow path of the respirator. A further important advantage of the invention is that the barriers can be exchanged at the same time in a simple manner for all medical components due to the carrier 20 that the barriers have in common.

Although modifications and changes may be suggested by those skilled in the art, it is the intention of the inventors to embody within the patent warranted hereon all changes and modifications as reasonably and properly come within the scope of their contribution to the art.

We claim as our invention:

1. A barrier arrangement comprising:
   a carrier adapted to be disposed adjacent a measuring tube in a respirator flow path, said carrier having a substantially planar element with plurality of side-by-side openings therein, with each opening containing a barrier selected from the group consisting of moisture barriers and bacteria barriers; and
   said openings being positioned in said substantially planar element so that said barriers respectively therein are adapted to be disposed in front of components connected to said measuring tube.

2. A barrier arrangement as claimed in claim 1 wherein said carrier has an elongated form.

3. A barrier arrangement as claimed in claim 1 wherein said carrier has a periphery at which a seal is disposed that is adapted to be adjacent to said measuring tube.

4. A barrier arrangement as claimed in claim 1 wherein said barriers are selected from the group consisting of filters and membranes.

5. A respirator comprising:
   a flow path adapted to at least receive gas from a subject;
   a measuring tube in fluid communication with said flow path;
   a unit disposed adjacent to said measuring tube containing a plurality of measuring components rigidly mounted therein; and
   a carrier which is introducible between said measuring tube and said unit, said carrier having a plurality of opening therein with respective barriers in each of said openings, said barriers being selected from the group consisting of moisture barriers and bacteria barriers, and said openings and said respective barriers therein being disposed respectively directly in front of said measuring components in said unit.

6. A respirator as claimed in claim 5 wherein said carrier is exchangeable.

* * * * *